United States Patent [19]

Koletar et al.

[11] 4,190,657

[45] Feb. 26, 1980

[54] NAPHTHYRIDINE DERIVATIVES

[75] Inventors: Gabor I. Koletar, Le Plessis-Robinson; Henry Najer, Paris; Jean P. G. LeFevre, Paris; Régis Dupont, Paris; Don Pierre R. L. Giudicelli, Fontenay-sous-Bois; Claude C. H. Morel, Massy, all of France

[73] Assignee: Synthelabo, Paris, France

[21] Appl. No.: 786,557

[22] Filed: Apr. 11, 1977

[30] Foreign Application Priority Data

| Mar. 11, 1976 [FR] | France | 77 07248 |
| Apr. 13, 1976 [FR] | France | 76 10773 |
| Jun. 1, 1976 [FR] | France | 76 16445 |
| Oct. 27, 1976 [FR] | France | 76 32319 |
| Dec. 24, 1976 [FR] | France | 76 39035 |
| Mar. 11, 1977 [FR] | France | 77 07249 |

[51] Int. Cl.$^2$ ............... A61K 31/445; C07D 471/12
[52] U.S. Cl. .................................... 424/256; 546/66
[58] Field of Search ........... 260/295 A, 295 N, 295 B, 260/295 AM, 294.9, 296 P; 424/263, 256; 546/66

[56] References Cited

U.S. PATENT DOCUMENTS

| 3,299,078 | 1/1967 | Pachter | 260/296 P |
| 3,555,018 | 1/1971 | Davis | 260/296 P X |

OTHER PUBLICATIONS

Kimura et al., Chem. Abst., vol. 68, 1968, parag. 87551v.
Oehl et al., Chemical Berichte, 109, (705–709) 1976.
Kovach et al., Chemical Abstracts, vol. 73 (1970) 64634z.
Taborsky et al., Journal of Medicinal Chemistry, vol. 7 (1964), pp. 135–141.
Wieland et al., Chemical Abstracts, vol. 51, (1957) 7371c.

*Primary Examiner*—Richard Raymond
*Attorney, Agent, or Firm*—Stevens, Davis, Miller & Mosher

[57] ABSTRACT

The present invention relates to new indolo [3,2,1-de]-[1,5]naphthyridine derivatives and their addition salts with pharmaceutically acceptable acids, the preparation of such derivatives and salts and medicaments in which they are present as active principle.

13 Claims, No Drawings

NAPHTHYRIDINE DERIVATIVES

The present invention relates to new indolo[3,2,1-de][1,5]naphthyridine derivatives and their addition salts with pharmaceutically acceptable acids, the preparation of such derivatives and salts and medicaments in which they are present as active principle.

The invention provides naphthyridine derivatives in the form of racemates or optical isomers corresponding to the formula:

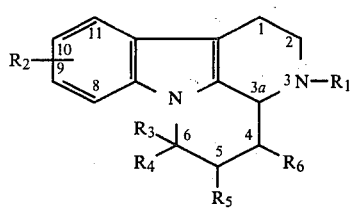

(I)

wherein $R_1$ represents a hydrogen atom or a group chosen from alkyl groups with 1 to 4 carbon atoms, 2-oxo-propyl, 2-hydroxy-propyl, 3-oxo-butyl, 3-hydroxy-butyl, cyclopropylmethyl, benzyl, halogenobenzyl (preferably fluorobenzyl or chlorobenzyl), acetyl, cyclopropylcarbonyl and benzoyl groups, and —$(CH_2)_n$—$R'$ groups where n is 1 or 2 and $R'$ represents a methoxycarbonyl, ethoxycarbonyl or cyano group, $R_2$ represents a hydrogen atom, a halogen atom, or a methyl or methoxy group, $R_6$ represents a hydrogen atom or a $COR_7$ group, $R_7$ being a hydroxyl group, an alkoxy group with 1 to 4 carbon atoms, or an amino, methylamino, dimethylamino or cyclopropylamino group, and either $R_3$ represents a methyl or ethyl group, $R_4$ represents a hydrogen atom or a hydroxyl group and $R_5$ represents a hydrogen atom, or $R_3$ and $R_4$ together represent an oxygen atom and $R_5$ represents a hydrogen atom, or $R_3$ represents a methyl or ethyl group and $R_4$ and $R_5$ together represent an additional carbon-carbon bond, with the exception of the compounds wherein $R_3$ and $R_4$ are oxygen, and either $R_1$ is H, $R_2$ is $CH_3O$ in the 10-position and $R_6$ is H, or $R_1$ is H, $R_2$ is H and $R_6$ is H, and the stereoisomers of the compounds for which $R_6$ is an alkoxycarbonyl group, and addition salts of the compounds (I) with pharmaceutically acceptable organic or inorganic acids.

The compounds of the formula (I) and their salts can be used as medicaments in human and veterinary medicine.

All the compounds of the invention have two optical isomers, namely the d and l isomers, since the carbon atom in the 3a position is in effect asymmetrical. In the examples below racemates of the compounds are obtained.

Furthermore, the compounds I for which $R_6$ is an alkoxycarbonyl radical exhibit cis/trans isomerism relative to the bond between positions 3a and 4, the cis and trans isomers being separable by column chromatography.

One group of valuable compounds consists of compounds for which $R_1$ is a hydrogen atom, an alkyl group with 1 to 4 carbon atoms, a 3-oxo-butyl group, a 3-hydroxy-butyl group, a 2-oxo-propyl group, a 2-hydroxy-propyl group or a methoxycarbonylethyl group, $R_2$ is a hydrogen atom, a halogen atom, a methyl group or a methoxy group, $R_6$ represents a hydrogen atom, a methoxycarbonyl group, an ethoxycarbonyl group, or a cyclopropylaminocarbonyl group, and $R_3$, $R_4$ and $R_5$ and the exceptions are as defined above.

Preferred compounds of the invention are those for which $R_3$ and $R_4$ together represent an oxygen atom and $R_5$ is a hydrogen atom.

The compounds of the invention may be prepared by a process wherein tryptamine or one of its derivatives of the formula:

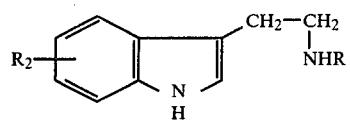

in which R is H, alkyl, cycloalkyl or optionally substituted benzyl, and $R_2$ has the meaning given above, is condensed with a carbonyl derivative of a diacid or its aliphatic diester, such as glutaric acid having a ketone group in the α-position or succinic acid having an aldehyde group in the α-position, thereafter cyclisation is carried out to form the indolo[3,2,1-de][1,5]naphthyridine nucleus, the substitution and/or degree of saturation of this nucleus being thereafter modified as desired by methods known per se.

The reaction schemes below show the principal methods for the preparation of the compounds of the formula (I).

CYCLISATION

Scheme $A_1$ - R= H

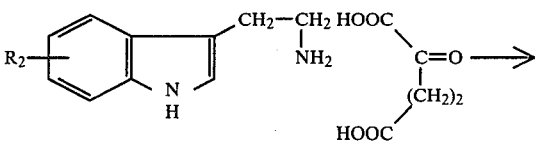

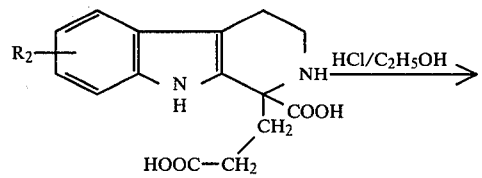

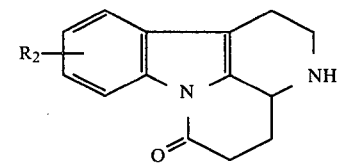

Scheme $A_2$ - $R_1$ = R  $R_6$ = $COR'_7$

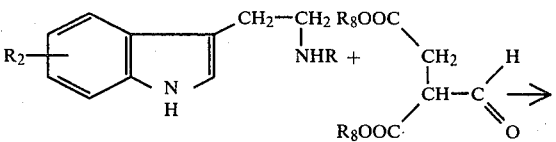

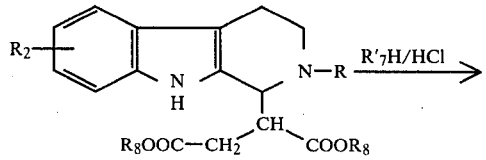

-continued
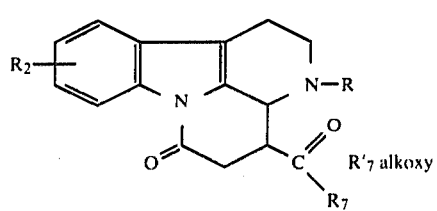
MODIFICATION OF THE BASIC RING
General Scheme
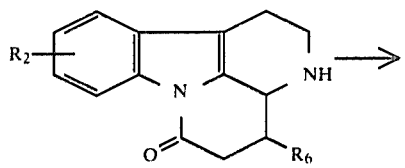
DETAILED PROCEDURES (VARIANTS)
Scheme B
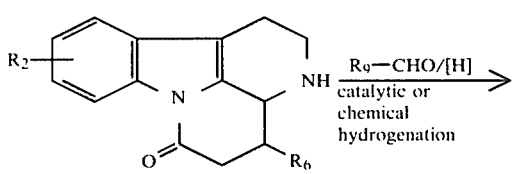
Scheme C
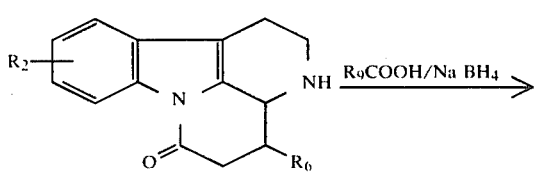
-continued
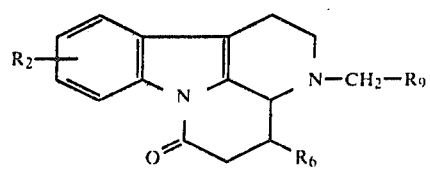
Scheme D
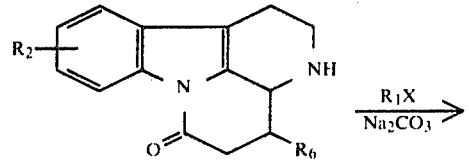
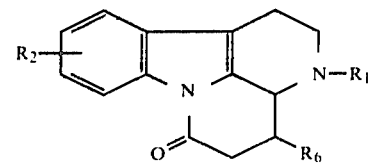
Scheme E
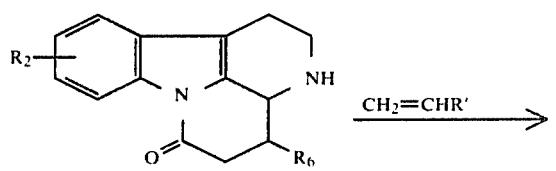
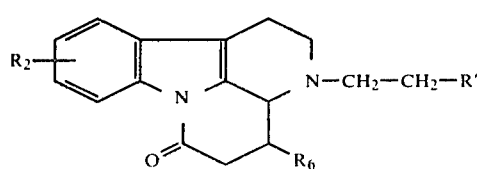
Scheme F
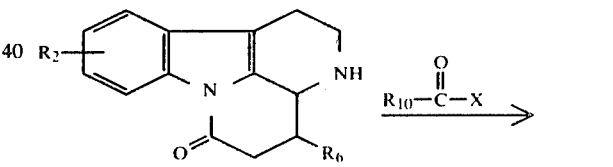
MODIFICATION OF SUBSTITUENTS OR OF THE DEGREE OF SATURATION
Scheme G
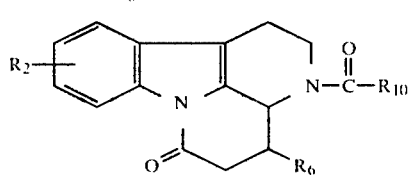
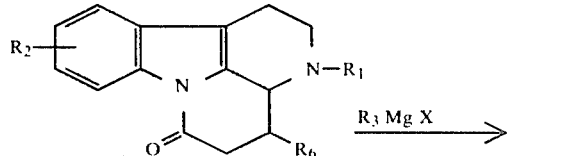
Scheme H
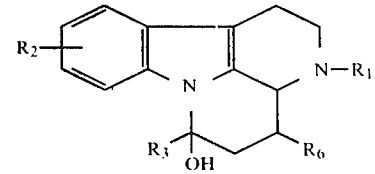

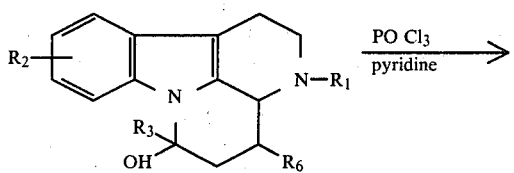

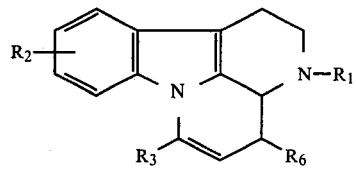

Scheme I

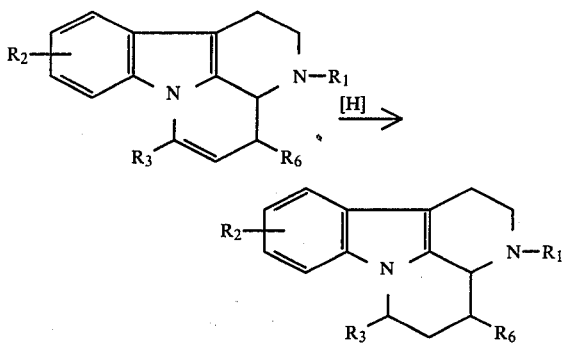

catalytic hydrogenation in tetrahydrofurane

Scheme J

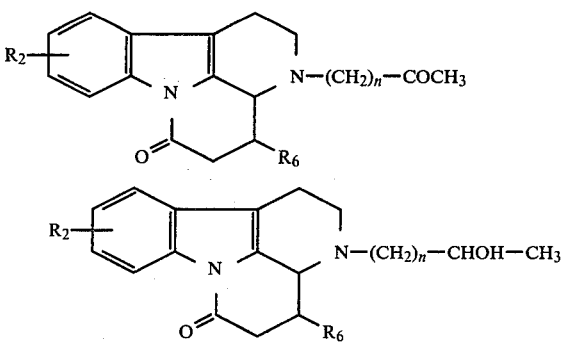

The reduction is preferably carried out in a low molecular weight alcohol, using an alkali metal borohydride, at ambient temperature.

The two diastereoisomers are separated by chromatography.

Scheme K

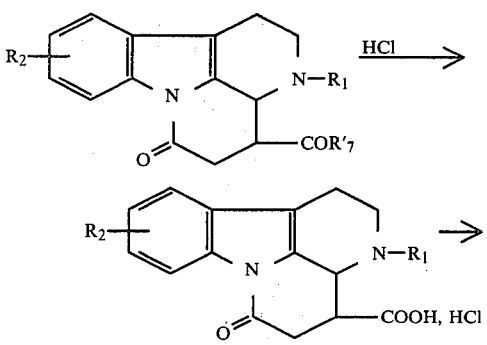

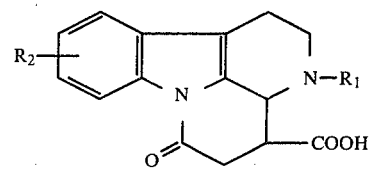

Hydrolysis of the ester and conversion of the acid hydrochloride to the non-salified free acid are carried out according to conventional methods.

Scheme L

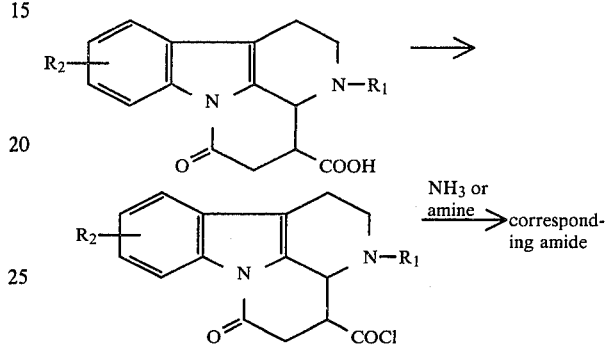

The acid chloride is preferably obtained using thionyl chloride and the conversion to the amide is carried out in the conventional way.

In the schemes above, $R_1$, $R_2$, $R_3$, $R_6$, $R_7$, $R'$ and n have the meanings already specified in connection with the formula (I), $R_8$ represents an alkyl radical with 1 to 4 carbon atoms, especially an ethyl radical, $R_9$ represents a hydrogen atom, an alkyl radical containing 1 to 3 carbon atoms, a cyclopropyl radical, a phenyl radical or a halophenyl radical, $R_{10}$ represents a methyl, cyclopropyl or phenyl radical and X represents a halogen atom, especially chlorine, bromine or iodine.

The non-limiting Examples below illustrate the way in which the invention is carried out and give details of the methods shown in schemes A to L.

The scheme $A_1$ method (1st cyclisation method) was substantially carried out in the way described by TABORSKY and Mc ISAACS (J. Med. Chem. 1964, 7, 135) for similar compounds. It is not reproduced here.

The IR and NMR spectra, as well as the analyses, confirm the structure of the compounds.

EXAMPLE 1

Methyl 1,2,3,3a,4,5-hexahydro-3-methyl-6-oxo-6H-indolo[3,2,1-de][1,5]naphthyridine-4-carboxylate and its methanesulphonate [Method $A_2$]

[$R_1$=CH$_3$, $R_2$=H, $R_3$+$R_4$=O, $R_5$=H and $R_6$=COOCH$_3$]

Cis and trans isomers 60 g (0.30 mol) of diethyl α-formyl-succinate, prepared according to the method described by PAYOT and CROB (Helv. Chim. Acta 1954, 37, 1269) or TOCANNE and ASSELINEAU (Bull. Soc. Chim. Fr. 1965, 3346), are added to a solution of 48 g (0.28 mol) of N$_6$-methyl-tryptamine in 2 l of benzene.

The solution obtained is stirred vigorously for one hour and then it is heated at the reflux temperature for 4 hours, removing the water formed by means of a Dean-Stark apparatus. After cooling, 1 liter of 3 N hydrochloric acid is added to the solution, the mixture is stirred very briskly for ¼ hour and subsequently it is rendered alkaline with a dilute solution of ammonia. The organic and aqueous phases are separated and the latter is extracted several times with ethyl acetate.

After combining the organic phases, they are washed several times with water and then dried over sodium sulphate and the solvent is evaporated under reduced pressure. 70 g, namely a yield of 65-70%, of an oil are thus obtained, which solidifies on scraping. The compound is a mixture of two isomers, namely cis and trans, as was shown by thin layer chromatography and the NMR spectrum. It is an intermediate diester, derived from 1,2,3,4-tetrahydro-3-methyl-pyrido-[3,4-b]indole

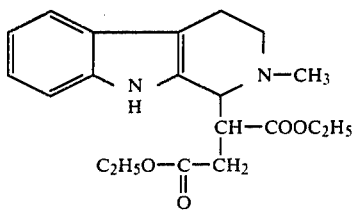

The crude compound is used for the stage which follows. However, a sample was purified for analysis, by recrystallisation from petroleum ether. It melts at 92° C.

A solution of 6 g (0.016 mol) of the above crude diester in 125 ml of methanol is introduced into a reaction apparatus under pressure. This solution is saturated at 0° with hydrogen chloride gas and then heated for 20 hours in an autoclave at 120° C.

After cooling, the reaction mixture is poured into a solution of ammonia and extracted several times with ethyl acetate. The extract is washed with water, dried over sodium sulphate and evaporated under reduced pressure. An oily residue is obtained which is chromatographed on a column of silica gel with methylene chloride containing 10 to 15% of acetone as the eluant.

The compound which is eluted first is the cis-3a,4-H,H isomer. It is obtained with a yield of 48 to 50%. It melts at 205° C.

The compound which is eluted second is the trans-3a,4-H,H isomer. It is obtained with a yield of 20 to 25%. It melts at 163° C.

One equivalent of methanesulphonic acid in solution in ethyl acetate is added dropwise to a solution of the cis isomer base in the same solvent.

After stirring for 30 minutes, the precipitate is filtered off and recrystallised from ethanol. Melting point >270° C. It is obtained with a yield of 75 to 85%.

In the same way the methane-sulphonate of the trans-isomer base is obtained, which melts at 257°-258° C.

EXAMPLE 2

Methyl 1,2,3,3a,4,5-hexahydro-6-oxo-6H-indolo[3,2,1-de][1,5-]naphthyridine-4-carboxylate (method A₂)

[R₁=R₂=H, R₃ and R₄=O, R₅=H and R₆=COOCH₃] cis and trans isomers 1. 23 g (0.14 mol) of tryptamine are dissolved hot in 100 ml of anhydrous methanol, the solution is cooled and then a solution of 30 g (0.15 mol) of diethyl α-formylsuccinate in 50 ml of anhydrous methanol is added dropwise with stirring. Stirring is maintained for 1 hour after the end of the addition, the solution is cooled to 0° and 75 ml of concentrated sulphuric acid (density=1.84) are added whilst maintaining the mixture at 0°.

The reaction is terminated by heating the reaction mixture for 1 hour at 100°. The reaction mixture is cooled, poured into 1.5 liters of iced water and filtered to remove a pinkish flocculent precipitate, and the filtrate is neutralised with 150 ml of 28% strength ammonia, in such a way that the internal temperature of the mixture does not exceed 10° to 15°. The precipitate which forms is extracted with methylene chloride and the combined organic extracts are washed with water and dried over anhydrous sodium sulphate. The extracts are filtered, the solvent is evaporated and the gummy residue (weight: 39 g, yield=98%) is chromatographed on two kilos of Merck silica (0.063-0.2) with a methylene chloride-acetone (7:3) mixture.

14 g (yield=37%) of a first product are collected, which melts at 166° C. and then, on eluting with acetone, 14.6 g (yield=38%) of a second product are collected, which melts at 195° C.

The nuclear magnetic resonance spectra show that the two compounds are geometric isomers, the isomer which melts at 166° having the trans-structure, whilst the isomer which melts at 195° has the cis-structure.

These are the cis- and trans-isomers of 4-methyl 1,2,3,3a,4,5-hexahydro-6-oxo-6H-indolo[3,2,1-de][1,5-]naphthyridine-carboxylate.

EXAMPLE 3

1,2,3,3a,4,5-Hexahydro-3-methyl-6H-indolo[3,2,1-de][1,5]naphthyridin-6-one and its methanesulphonate (method B)

[R₁=CH₃, R₂=H, R₃+R₄=O, R₅=R₆=H]

2.26 g (0.010 mol) of 1,2,3,3a,4,5-hexahydro-6H-indolo[3,2,1-de][1,5]naphthyridin-6-one (obtained in accordance with scheme A₁), 3 g (0.059 mol) of 98% strength formic acid and 2.5 g (0.024 mol) of 30% strength formaldehyde are introduced into a 50 ml flask, with stirring.

The solution obtained is heated to the reflux temperature and then left for 16 hours at the temperature of the laboratory. Thereafter, the reaction mixture is poured into 250 ml of water and the resulting mixture is washed twice, each time with 100 ml of benzene. The aqueous phase is rendered alkaline with sodium carbonate, which induces crystallisation.

The product is recrystallised from the minimum quantity of diisopropyl ether and 1.2 g of 1,2,3,3a,4,5-hexahydro-3-methyl-6H-indolo[3,2,1-de][1,5]naphthyridin-6-one are collected, melting at 95° C. The yield is about 50% and the structure was confirmed by the IR and NMR spectra.

In order to prepare the methanesulphonate, 5 g (0.0208 mol) of the above compound are suspended in 50 ml of methanol and 2.110 g (namely a 10% excess) of methanesulphonic acid are added. The solution obtained is stirred for 15 minutes and 500 ml of anhydrous diethyl ether are added dropwise thereto, which induces copious crystallisation. After stirring for one hour, the methane-sulphonate crystals are filtered off and recrystallised from the minimum quantity of isopropanol and 6.3 g of 1,2,3,3a,4,5-hexahydro-3-methyl-6H-indolo[3,2,1-de][1,5]napthyridin-6-one are collected, melting at 188°. The yield is 85%.

EXAMPLE 4

1,2,3,3a,4,5-Hexahydro-3-cyclopropylmethyl-6H-indolo[3,2,1-de][1,5-naphthyridin-6-one (method C)

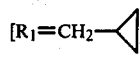

$R_2=H$, $R_3+R_4=O$, $R_5=R_6=H$]

A solution of 33.8 ml (0.430 mol) of cyclopropanecarboxylic acid in 500 ml of benzene is introduced into a 1 liter 3-necked flask, equipped with a stirrer, and 5 g (0.130 mol) of sodium borohydride are added to the solution, in small portions, in such a way that the temperature never exceeds 25° C. This addition operation requires about 4 hours. Thereafter, the mixture is left standing overnight at ambient temperature.

The next day, 5.5 g (0.0243 mol) of 1,2,3,3a,4,5-hexahydro-6H-indolo[3,2,1-de][1,5]naphthyridin-6-one are added to the above solution, all at once, and the mixture is heated for 5 hours at the reflux temperature.

After cooling, 500 ml of water and sufficient sodium carbonate to give an alkaline pH are added to the reaction mixture. The benzene phase is separated off, the aqueous phase is extracted twice, each time with 100 ml of benzene, and the extracts are combined with the original phase. This solution is washed with water, dried over sodium sulphate, filtered and concentrated to dryness. The residue is an oil which crystallises on the addition of diisopropyl ether. The product is recrystallised twice from the minimum quantity of this ether and 3.2 g of 1,2,3,3a,4,5-hexahydro-3-cyclopropylmethyl-6H-indolo[3,2,1-de][1,5]naphthyridin-6-one are collected, melting at 126° C.

Thin layer chromatography reveals a single spot.

EXAMPLE 5

1,2,3,3a,4,5-Hexahydro-3-(2-cyano-ethyl)-6H-indolo[3,2,1-de][1,5]naphthyridin-6-one (methods D and E)

[$R_1=-CH_2-CH_2-C\equiv N$, $R_2=H$, $R_3+R_4=O$, $R_5=R_6=H$]

(1) Method D 5 g (22 millimols) of 1,2,3,3a,4,5-hexahydro-6H-indolo[3,2,1-de][1,5]naphthyridin-6-one in solution in 100 ml of methyl ethyl ketone are introduced into a 250 ml flask with stirring, together with 4.7 g (44 millimols) of sodium carbonate, and the mixture is heated under reflux for 1 hour. 8 g (60 millimols) of bromopropionitrile and 5 g (30 millimols) of potassium iodide are then added to this suspension which is maintained under reflux for a further 48 hours. The reaction mixture is cooled, the inorganic salts are filtered off, the filtrate is evaporated to dryness and a residue is obtained which, after passing through a column of 140 g of Merck 7734 silica gel in a 7:3 mixture of the solvents benzene and EtOH, provides 4.3 g of a compound which melts at about 155° C.

After 2 recrystallisations, namely hot and cold, 2.7 g (yield 44%) of 1,2,3,3a,4,5-hexahydro-3-(2-cyanoethyl)-6H-indolo[3,2,1-de][1,5]naphthyridin-6-one, melting at 156°–157° C., are isolated.

(2) Method E 4.52 g (0.020 mol) of 1,2,3,3a,4,5-hexahydro-6H-indolo[3,2,1-de][1,5]naphthyridin-6-one, in suspension in 30 ml of anhydrous ethanol and 3 ml of acrylonitrile are introduced, under an atmosphere of nitrogen, into a 100 ml flask equipped with a stirrer.

The mixture is maintained for 24 hours at the reflux temperature. On cooling, crystallisation is observed. The precipitate is filtered off and recrystallised from the minimum quantity of anhydrous ethanol. 3.4 g of 1,2,3,3a,4,5-hexahydro-3-(2-cyano-ethyl)-6H-indolo[3,2,1-de][1,5]naphthyridin-6-one, melting at 157°–158°, are collected. This compound has the same properties as that obtained by method D.

EXAMPLE 6

1,2,3,3a,4,5-Hexahydro-3-benzoyl-6H-indolo[3,2,1-de][1,5]naphthyridin-6-one (method F)

[$R_1=C_6H_5CO$, $R_2=H$, $R_3+R_4=O$, $R_5=R_6=H$]

4 g (0.017 mol) of 1,2,3,3a,4,5-hexahydro-6H-indolo[3,2,1-de][1,5]naphthyridin-6-one in 100 ml of anhydrous tetrahydrofurane, 2 ml of pyridine and 4 ml of benzoyl chloride are introduced into a 250 ml flask and the mixture is stirred for 16 hours at 20°.

The pyridine hydrochloride which forms during the reaction is filtered off and then the filtrate is washed with water until the washing waters are neutral. The filtrate is then dried over sodium sulphate, filtered and evaporated to dryness. The crystals obtained are taken up in petroleum ether and then recrystallised from the minimum quantity of methanol. 4.8 g (yield 82%) of 1,2,3,3a,4,5-hexahydro-3-benzoyl-6H-indolo[3,2,1-de][1,5]naphthyridin-6-one, melting at 171°–172° C., are collected.

EXAMPLE 7

1,2,3,3a,4,5-Hexahydro-3,6-dimethyl-6-hydroxy-6H-indolo[3,2,1-de][1,5]naphthyridine (method G)

[$R_1=CH_3$, $R_2=H$, $R_3=CH_3$, $R_4=OH$, $R_5=R_6=H$]

Methyl-magnesium iodide is prepared in the usual way starting from 5 g of magnesium turnings, 75 ml of anhydrous diethyl ether and 11 ml (25 g or 0.420 mol) of methyl iodide.

5 g (0.028 mol) of 1,2,3,3a,4,5-hexahydro-3-methyl-6H-indolo[3,2,1-de][1,5]naphthyridin-6-one in solution in 50 ml of anhydrous tetrahydrofurane are added dropwise, under an atmosphere of nitrogen and at a rate such that the temperature does not exceed 5°, to the solution obtained, which is cooled to 0°. When the introduction operation is terminated, the reaction mixture is again stirred for 1 hour 30 minutes at 0°, then the excess magnesium is destroyed by slowly adding iced water and finally the mixture is poured into 1,000 ml of water saturated with ammonium chloride, which induces crystallisation. The compound is recrystallised from the minimum quantity of ethyl acetate and 2.5 g (yield 47%) of 1,2,3,3a,4,5-hexahydro-3,6-dimethyl-6-hydroxy-6H-indolo[3,2,1-de][1,5]naphthyridine are collected, melting at 194°.

EXAMPLE 8

1,2,3,3a-Tetrahydro-3,6-dimethyl-4H-indolo[3,2,1-de][1,5]naphthyridine (method H)

[$R_1=CH_3$, $R_2=H$, $R_3=CH_3$, $R_4$ and $R_5=$ an additional bond and $R_6=H$]

4 g (0.0156 mol) of 1,2,3,3a,4,5-hexahydro-3,6-dimethyl-6-hydroxy-6H-indolo[3,2,1-de][1,5]naphthyridine, 60 ml of anhydrous benzene and 60 ml of pyridine are stirred in a 250 ml flask, until a solution is obtained, and 4 ml of phosphorus oxychloride are added. The flask is then closed with a calcium chloride guard tube. Stirring is continued for 2 hours at 25° and the precipitate obtained is poured into 1,500 ml of water.

The organic phase is decanted off, the aqueous phase is extracted twice, each time with 200 ml of benzene, and the organic solutions are combined, washed with water, dried over sodium sulphate, filtered and finally evaporated to dryness. A resin is thus obtained which is first treated with petroleum ether, it is then recrystallised from the minimum quantity of diisopropyl ether and 1.2 g (yield 32%) of 1,2,3,3a-tetrahydro-3,6-dimethyl-4H-indolo[3,2,1-de][1,5]naphthyridine, melting at 89°, are collected.

EXAMPLE 9

N-Cyclopropyl-1,2,3,3a,4,5-hexahydro-6-oxo-6H-indolo[3,2,1-de][1,5]naphthyridine-4-carboxamide (method L)

[$R_1 = R_2 = H$, $R_3$ and $R_4 = O$, $R_5 = H$,

  ]

0.011 mol of anhydrous pyridine (namely 0.9 ml) is added to 3 g of 1,2,3,3a,4,5-hexahydro-6-oxo-6H-indolo[3,2,1-de][1,5]naphthyridine-4-carboxylic acid (cis-isomer prepared in accordance with scheme K) in suspension in 100 ml of dichloroethane. The reaction flask is plunged into an ice bath. After a few moments, 1 ml of thionyl chloride (0.011 mol) is added, the flask is withdrawn from the ice bath and the mixture is stirred for 2 hours 30 minutes at normal temperature (with a calcium chloride guard tube).

Thereafter 0.33 mol of cyclopropylamine (about 22 ml) is added and the mixture is again stirred for 2 hours 30 minutes. Finally, after the addition of a solution of 100 ml of 0.5 N $NH_4OH$, the mixture is stirred and decanted, and the aqueous solution is extracted 3 times, each time with 100 ml of methylene chloride. The organic solutions are combined, washed with water, dried over sodium sulphate and evaporated, after filtration.

800 mg of N-cyclopropyl-1,2,3,3a,4,5-hexahydro-6-oxo-6H-indolo[3,2,1-de][1,5]naphthyridine-4-carboxamide are collected, melting at 230° C.

EXAMPLE 10

Methyl 1,2,3,3a,4,5-hexahydro-6-oxo-10-fluoro-6H-indolo[3,2,1-de][1,5]naphthyridine-4-carboxylate (method A₂)

[$R_1 = H$, $R_2 = 10\text{-F}$, $R_3$ and $R_4 = O$, $R_5 = H$, $R_6 = COOCH_3$-2 stereoisomers].

5-Fluoro-tryptamine is liberated by shaking, in a separating funnel, a suspension of 9.1 g (0.042 mol) of 5-fluoro-tryptamine hydrochloride in water and ether, in the presence of dilute ammonia. The phases are separated and the ether phase is washed with water and then dried over $Na_2SO_4$. The ether is evaporated in vacuo. Traces of water are removed by distillation with benzene in vacuo. The resulting oil is dissolved in 150 cm³ of anhydrous ether. 10 g of molecular sieve 4 A (Merck) are introduced and then 9 g (0.044 mol) of diethyl α-formylsuccinate are added. The reaction mixture is maintained at ambient temperature for one night, with stirring. The sieve is removed by filtration. A current of hydrogen chloride gas is bubbled through the filtrate, which induces a light chestnut-coloured gummy precipitation which solidifies slowly as white crystals. The mixture is stirred for 30 minutes after the end of the bubbling operation and then the ether is removed by suction. The precipitate is suspended in 50 cm³ of anhydrous methanol and 25 cm³ of concentrated $H_2SO_4$ are added with stirring. The mixture is heated at 100° C. for 1 hour. The mixture is cooled by immersion in a bath of iced water and then poured into crushed ice. The pH of the mixture is made alkaline by the addition of the required quantity of ammonia. The mixture is extracted with methylene chloride, washed with water, dried over $Na_2SO_4$ and then evaporated in vacuo. 9.1 g of a solid residue are obtained (yield 70%).

This is chromatographed on 600 g of silica gel (Merck 60, 0.063 - 0.2 mm) in a 7:3 mixture of methylene chloride and acetone.

The least polar product, compound A, represents 3.6 g (yield 27%).

The most polar product, compound B, represents 2.8 g (yield 21%).

Compounds A and B are separately recrystallised from the minimum quantity of ethyl acetate. A provides 2.8 g (yield 22%) of the expected compound, melting point = 172° C. It corresponds to the trans-$H_{3a}$-$H_4$ isomer. B provides 1.9 g (yield 15%), melting point = 214° C. It corresponds to the cis-$H_{3a}$-$H_4$ isomer.

TABLE I

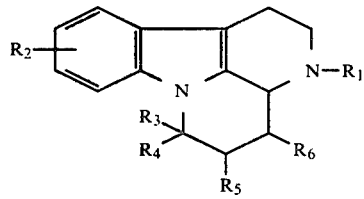

| Compound No. | $R_1$ | $R_2$ | $R_3$ | $R_4$ | $R_5$ | $R_6$ | Method | Base or Salt | Characteristics Melting point (°C.) |
|---|---|---|---|---|---|---|---|---|---|
| 1 (Example 1) | $CH_3$ | H | | O | H | $COOCH_3$ | $A_2$ | m.s. cis | >270 |
| | | | | | | | | m.s. trans | 257-258 |
| 2 (Example 3) | $CH_3$ | H | | O | H | H | B | base | 95 |
| | | | | | | | | m.s. | 188 |
| 3 | $C_2H_5$ | H | | O | H | H | B | base | 114 |

TABLE I-continued

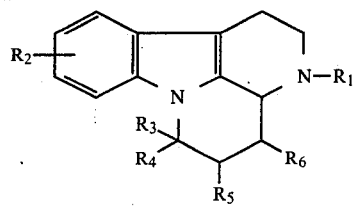

| Compound No. | $R_1$ | $R_2$ | $R_3$ | $R_4$ | $R_5$ | $R_6$ | Method | Base or Salt | Characteristics Melting point (°C.) |
|---|---|---|---|---|---|---|---|---|---|
| 4 (Example 4) | $CH_2-\triangleleft$ | H | | O | H | H | C | base | 126 |
| 5 | $C_6H_5CH_2$ | H | | O | H | H | D | base m.s. | 174 227–230 |
| 6 (Example 5) | $CH_2CH_2CN$ | H | | O | H | H | DE | base | 156 |
| 7 (Example 6) | $C_6H_5CO$ | H | | O | H | H | F | base | 171–2 |
| 8 (Example 7) | $CH_3$ | H | $CH_3$ | OH | H | H | G | base | 194 |
| 9 (Example 8) | $CH_3$ | H | $CH_3$ | bond | | H | H | base | 89 |
| 10 | $CH_3$ | H | $CH_3$ | H | H | H | I | base | 110 |
| 11 | H | $CH_3(10)$ | | O | H | H | $A_1$ | base | 170–2 |
| 12 | $n-C_3H_7$ | H | | O | H | H | B | base | 111–113 |
| 13 | $i-C_3H_7$ | H | | O | H | H | D | base | 161 |
| 14 | $CH_3CO$ | H | | O | H | H | F | base | 174 |
| 15 | $\triangleleft-CO$ | H | | O | H | H | F | base | 134 |
| 16 | $-CH_2-C_6H_4-F$ (ortho) | H | | O | H | H | D | base | 160 |
| 17 | $-CH_2-C_6H_4-F$ (para) | H | | O | H | H | D | base | 165 |
| 18 | $-CH_2-C_6H_4-Cl$ | H | | O | H | H | D | base | 148 |
| 19 | $-CH_2-CH_2-COOCH_3$ | H | | O | H | H | E | base | 122–125 |
| 20 | $CH_3$ | $CH_2(10)$ | | O | H | H | B | base | 108–109 |
| 21 | $C_2H_5$ | H | $CH_3$ | OH | H | H | C | base | 193–194 |
| 22 | $n-C_3H_7$ | H | $CH_3$ | OH | H | H | G | base | 210 |
| 23 | $CH_3$ | H | $C_2H_5$ | OH | H | H | G | base | 190 |
| 24 | $-CH_2-\triangleleft$ | H | $CH_3$ | OH | H | H | G | base | 175 |
| 25 | $-CH_2-C_6H_5$ | H | $CH_3$ | OH | H | H | G | base | 175–177 |
| 26 | $C_2H_5$ | H | $CH_3$ | Bond | | H | H | base | 89 |
| 27 | $-CH_2-\triangleleft$ | H | $CH_3$ | Bond | | H | H | base | 74 |
| 28 | $C_2H_5$ | H | $CH_3$ | H | H | H | I | base m.s. | 106 215 |
| 29 | $-CH_2-\triangleleft$ | H | $CH_3$ | H | H | H | I | | |
| 30 | $CH_3$ | H | | O | H | $-COOC_2H_5$ | $A_2$ | base m.s. (3a,4H,H-cis) base (3a,4-H,H-trans | 162 250 116 |
| 31 | $CH_3$ | H | | O | H | $-COO-n-C_3H_7$ | $A_2$ | base m.s. (3a,4-H,H-cis) | 150 252 |
| 32 | $CH_3$ | H | | O | H | $-COO-n-C_4H_9$ | $A_2$ | base | 135 |
| 33 | $CH_2CH_2COCH_3$ | H | | O | H | H | E | base | 100 |
| 34 | $CH_2COOC_2H_5$ | H | | O | H | H | D | m.s. | 203 |
| 35 | $CH_2CH_2CHOHCH_3$ | H | | O | H | H | J | base, isomer A base, isomer B | 144 115 |
| 36 | H | H | | O | H | COOH | K | base | >250 |
| 37 (Example 9) | H | H | | O | H | $CONH-\triangleleft$ | | | |
| 38 | $CH_3$ | $CH_3O(10)$ | | O | H | H | B | m.s. | 245–6 |
| 39 (Example 2) | H | H | | O | H | $COOCH_3$ | $A_2$ | base (3a,4-H,H cis) | 195 |

TABLE I-continued

| Compound No. | R₁ | R₂ | R₃ | R₄ | R₅ | R₆ | Method | Base or Salt | Characteristics Melting point (°C.) |
|---|---|---|---|---|---|---|---|---|---|
| 40 | H | H | | O | H | —COOC₂H₅ | A₂ | m.s. (3a,4-H,H trans) | 261 |
|  |  |  |  |  |  |  |  | m.s. (3a,4-H,H cis) | 243 |
| 41 | C₂H₅ | H | | O | H | —COOCH₃ | D | m.s. (3a,4-H,H trans) | 268 |
|  |  |  |  |  |  |  |  | m.s. (3a,4-H,H cis) | 223 |
| 42 | C₂H₅ | H | | O | H | —COO C₂H₅ | D | m.s. (3a,4-H,Hcis) | 231 |
| 43 | CH₂—△ | H | | O | H | —COO CH₃ | D | m.s. | 220 |
| 44 | CH₃ | H | | O | H | COOH | K | (3a,4-H,Hcis) base | 280 |
| 45 | CH₃ | H | | O | H | —CO NH₂ | L | (3a,4-H,Hcis) base | >280 |
| 46 | CH₃ | H | | O | H | —CO NH CH₃ | L | (3a,4-H,Hcis) base | 182 |
| 47 | CH₃ | H | | O | H | —CO N(CH₃)₂ | L | (3a,4-H,Hcis) base | 251 |
| 48 | CH₃ | H | | O | H | —CO NH—△ | L | (3a,4-H,Hcis) base | 170 |
| 49 | —CH₂CH₂COCH₃ | H | | O | H | —COO CH₃ | E | (3a,4-H,Hcis) m.s. | 173 |
|  |  |  |  |  |  |  |  | (3a,4-H,Hcis) m.s. | 160 |
| 50 | —CH₂—CH₂—CH(OH)—CH₃ | H | | O | H | —COO CH₃ | J | (3a,4-H,Htrans) base | 231 |
|  |  |  |  |  |  |  |  | (3a,4-H,Hcis) isomer A base | 198 |
|  |  |  |  |  |  |  |  | (3a,4-H,Hcis) isomer B base | 198 |
| 51 | H | Cl(10) | | O | H | COO CH₃ | D | (3a,4-H,Htrans) base | 191 |
| 52 | H | Cl(10) | | O | H | H | A₁ | base | 161-3 |
| 53 | CH₃ | Cl(10) | | O | H | H | B | base | 118-9 |
| 54 | H | F(10) | | O | H | H | A₁ | base | 123-5 |
| 55 | CH₃ | F(10) | | O | H | H | B | base | 146-7 |
| 56 | —CH₂—CH₂COCH₃ | Cl(10) | | O | H | H | E | base | 135-6 |
| 57 | —CH₂—CH₂COCH₃ | F(10) | | O | H | H | E | base | 124-5 |
| 58 | H | Cl(10) | | O | H | —COOCH₃ | A₂ | base | 162 |
|  |  |  |  |  |  |  |  | (3a,4-H-trans) base | 209 |
| 59 (Example 10) | H | F(10) | | O | H | —COOCH₃ | A₂ | (3a,4-H-cis) base | 172 |
|  |  |  |  |  |  |  |  | (3a,4-H,-trans) base | 214 |
| 60 | CH₃ | F(10) | | O | H | —COOCH₃ | B | (3a,4-H-cis) base | 189 |
|  |  |  |  |  |  |  |  | (3a,4-H,trans) base | 237 |
| 61 | CH₃ | Cl(10) | | O | H | —COOCH₃ | B | (3a,4-H-cis) base | 215 |
|  |  |  |  |  |  |  |  | (3a,4-H-trans) base | 270 |
| 62 | CH₂COCH₃ | H | | O | H | H | D | (3a,4-H-cis) base | 135-6 |
| 63 | CH₂CHOHCH₃ | H | | O | H | H | J | base (isomer A) | 164,5-165,5 |
|  |  |  |  |  |  |  |  | base (isomer B) | 142-143 |

TABLE I-continued

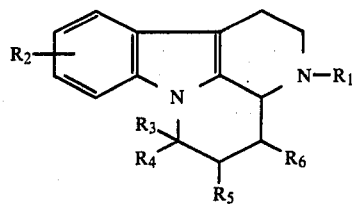

| Compound No. | R₁ | R₂ | R₃ | R₄ | R₅ | R₆ | Method | Base or Salt | Characteristics Melting point (°C.) |
|---|---|---|---|---|---|---|---|---|---|
| 64 | $CH_2-CH_2-COCH_3$ | $-CH_{3(10)}$ | O | | H | H | D | base | 120-1 |
| 65 | H | $-Cl\ (11)$ | O | | H | H | Al | base | 145-6 |
| 66 | $CH_3$ | $-Cl\ (9)$ | O | | H | H | B | base | 168-9 |
| 67 | $CH_2CH_2COOCH_3$ | $-F\ (10)$ | O | | H | H | D | base | 140-42 |
| 68 | $CH_2CH_2COOCH_3$ | $-Cl\ (10)$ | O | | H | H | D | base | 113-4 |
| 69 | $CH_3$ | $-CH_{3(9)}$ | O | | H | H | B | base | 145-51 (d) |
| 70 | $C_2H_5$ | $-Cl\ (10)$ | O | | H | H | D | base | 124-5 |
| 71 | $CH_2-C_6H_5$ | H | $-CH_3$ | BOND | H | H | | base | 64-7 |
| 72 | H | $-CL\ (9)$ | O | | H | H | Al | base | 195-6 |
| 73 | H | $-CH_3(8)$ | O | | H | H | Al | base | 76-8 | m.s. = methanesulphonate

The compounds of the invention have been subjected to a pharmacological study.

1. TOXICITY

The 50 percent lethal dose ($LD_{50}$) of the compounds is determined for mice of strain CD 1 by a graphical method.

The results are indicated in Table II below, for a representative number of compounds.

2. ANOXIA DUE TO PRESSURE REDUCTION

Mice of the CD 1 strain are kept in an atmosphere depleted in oxygen, by setting up a partial vacuum (190 mm. of mercury, corresponding to 5.25% of oxygen).

The survival time of the animals is noted. This time is increased by the agents capable of favouring oxygenation in the tissues and, in particular, in the brain. The compounds studied are administered intraperitoneally in several doses 10 minutes before the experiment. The percentage increases of the survival time relative to the values obtained with control animals are calculated. The mean active dose (MAD), namely the dose which increases the survival time by 100%, is determined graphically.

The results are indicated in Table II below for a representative number of compounds.

3. ACTION ON THE DURATION OF THE "SLEEP" INDUCED BY SODIUM 4-HYDROXY-BUTYRATE

This action was determined from the influence of the compounds on the duration of the "sleep" induced by sodium 4-hydroxy-butyrate (GHB) in curarised rats.

The animals used are male rats of the Charles River strain, weighing 200±20 g. The animals, curarised by alloferin given intraperitoneally at the rate of 1 mg/kg, are placed under artificial respiration by means of a mask applied over the snout (respiration frequency: 40/minute; volume respired: 14 cc). The oesophagus is ligatured beforehand so as to avoid air entering the stomach.

Fronto-parietal and occipital cortical electrodes make it possible to record the electrocorticographic activity on a Grass model 79P polygraph at a speed of 6 mm/sec. The animals are prepared under local anaesthesia (2% xylocaine). The rats are kept at a constant temperature (37.5° C.) throughout the experiment. Ten minutes after the end of the preparation of the rat, a dose of 200 mg/kg of Na 4-hydroxybutyrate is injected intravenously into the tail.

Doses of 10 and 30 mg/kg of the compounds to be studied are administered intraperitoneally 3 minutes after the administration of the sodium 4-hydroxy-butyrate.

The traces are evaluated for periods of 15 minutes over the course of 75 minutes after the injection of "GHB". During this period of analysis, the total duration of the "sleep" is determined. A series of 15 comparisons makes it possible precisely to define the duration of the "GHB sleep".

The statistical analysis of the results is carried out with the aid of the Mann-Whitney "U" test.

The results are reported in Table III below.

TABLE II

| COMPOUND | ACUTE TOXICITY $LD_{50}$ (mg/kg) for intraperitoneal administration | ANOXIA DUE TO PRESSURE REDUCTION intraperitoneal administration |
|---|---|---|
| 2 (base) | 85 | 6 |
| 2 (m.s.) | 52 | 4.5 |
| 9 | 78 | 6.5 |
| 3 | 58 | 9 |
| 10 | 50 | 6.5 |
| 21 | 75 | 7 |
| 26 | 67 | 10 |
| 22 | 105 | 8 |
| 28 (m.s.) | 40 | 4.5 |
| 30 (m.s.) | 110 | 9 |
| 1 (m.s.cis) | 170 | 4 |
| 33 | 170 | 8 |
| 35 (base, isomer A) | 150 | 9 |
| 38 | 65 | 8 |
| 52 | 165 | 9.5 |
| 53 | 150 | 8 |
| 62 | 190 | 10 |

TABLE III

| COMPOUND | TOXICITY (mg/kg) intravenous | TOXICITY (mg/kg) intraperitoneal | ACTIVITY number of animals | ACTIVITY dose, mg/kg, given intraperitoneally | TOTAL DURATIN in minutes. seconds | DIFFERENCE IN % RELATIVE TO THE CONTROLS |
|---|---|---|---|---|---|---|
| COMPARISON | | | 15 | — | 54.12 ± 2.07 | — |
| 11 | 105 | 155 | 6 | 30 | 34.08 ± 1.21 | −37 |
| 19 m.s. | 103 | 680 | 6 | 30 | 38.59 ± 1.20 | −28 |
| 1 trans m.s. | 47 | 185 | 3 | 40 | 32.01 ± 2.59 | −41 |
| 49 m.s.cis | — | 600 | 6 | 30 | 38.51 ± 3.12 | −28 |
| | | | 6 | 10 | 35.22 ± 2.26 | −35 |
| 52 | 110 | 165 | 6 | 30 | 32.35 ± 5.02 | −40 |
| | | | 6 | 10 | 37.34 ± 3.35 | −31 |
| 54 | — | 100 | 6 | 30 | 28.28 ± 4.28 | −47 |
| | | | 6 | 10 | 40.01 ± 5.00 | −26 |
| 56 | — | 575 | 6 | 30 | 30.39 ± 3.01 | −43 |
| | | | 6 | 10 | 43.07 ± 3.26 | −20 |
| 51 | — | 760 | 6 | 30 | 37.51 ± 2.12 | −30 |
| 63 isomer A | 75 | 125 | 6 | 30 | 34.52 ± 2.14 | −36 |
| 58 cis-isomer | — | 190 | 6 | 30 | 36.08 ± 2.47 | −33 |
| 58 trans-isomer | — | 170 | 6 | 30 | 31.12 ± 2.18 | −42 |
| 60 cis-isomer | — | 725 | 6 | 10 | 34.22 ± 2.47 | −37 |
| 65 | — | 54 | 6 | 10 | 34.51 ± 1.42 | −36 |
| 69 | — | 88 | 6 | 10 | 29.46 ± 1.27 | −45 |

The pharmacological study of the compounds of the invention shows that they are active in the test on anoxia due to pressure reduction, in mice, whilst only being slightly toxic and that they exert a significant wakening action in the test on "sleep" induced by sodium 4-hydroxy-butyrate.

The compounds of the invention, which possess both an anti-anoxia activity and a psychotropic activity, can be used in therapy for the treatment of disturbances of alertness, in particular to combat disturbances of behaviour attributable to damage to the cerebral vessels and to cerebral sclerosis in geriatrics, as well as for the treatment of absence due to cranial traumatisms, and the treatments of states of depression.

The invention consequently comprises all pharmaceutical compositions which contain the compounds and/or their salts as active principles, in association with any excipient appropriate for their administration, in particular their oral or parenteral administration.

The methods of administration can be oral and parenteral.

The daily posology can range from 10 to 100 mg.

We claim:

1. A compound of the formula:

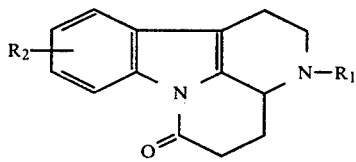

wherein
R₁ is —(C$_{1-2}$alkylene)COO(C$_{1-2}$alkyl) or —(C$_{1-2}$alkylene)CO(C$_{1-2}$alkyl); or hydrogen;
R₂ is hydrogen, halogen, methyl, or methoxy;
provided that when R₁ is hydrogen, R₂ is neither hydrogen nor 10-methoxy in the form of a racemate or optical isomer thereof, or a pharmaceutically acceptable salt of said compound.

2. A compound of the formula

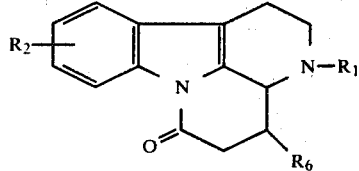

wherein
R₁ is hydrogen, alkyl of 1 to 4 carbon atoms, 3-oxobutyl, 3-hydroxybutyl, 2-oxopropyl, 2-hydroxypropyl or methoxycarbonylethyl;
R₂ is hydrogen, halogen, methyl or methoxy; and
R₆ is methoxycarbonyl, ethoxycarbonyl or cyclopropyl-aminocarbonyl;
in the form of a racemate or optically active form thereof, or a pharmaceutically acceptable salt of said compound.

3. A compound of claim 2, wherein R₂ is chlorine or fluorine.

4. 1,2,3,3a,4,5-Hexahydro-3-(3-oxo-butyl)-6-oxo-6H-indolo[3,2,1-de][1,5]naphthyridine or a pharmaceutically acceptable salt thereof.

5. 1,2,3,3a,4,5-Hexahydro-3-(2-oxo-propyl)-6-oxo-6H-indolo[3,2,1-de][1,5]naphthyridine or a pharmaceutically acceptable salt thereof.

6. 1,2,3,3a,4,5-Hexahydro-6-oxo-10-chloro-6H-indolo[3,2,1-de][1,5]naphthyridine or a pharmaceutically acceptable salt thereof.

7. 1,2,3,3a,4,5-Hexahydro-6-oxo-10-fluoro-6H-indolo[3,2,1-de][1,5]naphthyridine or a pharmaceutically acceptable salt thereof.

8. A pharmaceutical composition capable of providing an anti-anoxia or a psychotropic effect, which comprises an amount of a compound of claim 1 capable of providing said effect.

9. A method of providing a subject with an anti-anoxia effect which comprises treating said subject with an amount of a compound of claim 1 capable of providing said anti-anoxia effect.

10. A method of providing a subject with psychotropic effect which comprises treating said subject with an amount of a compound of claim 1 capable of providing said psychotropic effect.

11. A method of providing a subject with an anti-anoxia effect which comprises treating said subject with an amount of a compound of claim 2 capable of providing said anti-anoxia effect.

12. A method of providing a subject with an anti-anoxia effect which comprises treating said subject with an amount of 1,2,3,3a,4,5-Hexahydro-3-(3-oxo-butyl)-6-oxo-6-6H-indolo[3,2,1-de][1,5]naphthyridine capable of providing said anti-anoxia effect.

13. A method of providing a subject with an anti-anoxia effect which comprises treating said subject with an amount of 1,2,3,3a,4,5-Hexahydro-6-oxo-10-chloro-6H-indolo[3,2,1-de][1,5]naphthyridine capable of providing said anti-anoxia effect.

* * * * *

UNITED STATES PATENT AND TRADEMARK OFFICE
CERTIFICATE OF CORRECTION

PATENT NO. : 4,190,657

DATED : February 26, 1980

INVENTOR(S) : KOLETAR ET ALL

It is certified that error appears in the above-identified patent and that said Letters Patent are hereby corrected as shown below:

Column 1, in "Foreign Application Priority Data" change the date March 11, 1976 of french patent No. 7707248 to read --March 11, 1977--.

Signed and Sealed this

Fifteenth Day of July 1980

[SEAL]

Attest:

SIDNEY A. DIAMOND

Attesting Officer

Commissioner of Patents and Trademarks